United States Patent [19]
Yoshida

[11] Patent Number: 6,135,596
[45] Date of Patent: Oct. 24, 2000

[54] OPHTHALMIC APPARATUS

[75] Inventor: Makoto Yoshida, Gamagori, Japan

[73] Assignee: Nidek Co., Ltd., Gamagori, Japan

[21] Appl. No.: 09/232,643

[22] Filed: Jan. 19, 1999

[30] Foreign Application Priority Data

Jan. 20, 1998 [JP] Japan .................................. 10-023844

[51] Int. Cl.$^7$ ..................................................... A61B 3/10
[52] U.S. Cl. ............................................................. 351/200
[58] Field of Search .................................... 351/200, 205, 351/206, 208, 211, 212, 221, 245, 246

[56] References Cited

U.S. PATENT DOCUMENTS

| | | | |
|---|---|---|---|
| 4,779,973 | 10/1988 | Miller et al. | 351/212 |
| 5,279,300 | 1/1994 | Miwa et al. | |
| 5,302,979 | 4/1994 | Maeda et al. | |
| 5,406,076 | 4/1995 | Mimura et al. | |
| 5,502,251 | 3/1996 | Katou | |
| 5,610,672 | 3/1997 | Hirono et al. | |
| 5,644,375 | 7/1997 | Suzuki | |
| 5,696,573 | 12/1997 | Miwa | |
| 5,907,388 | 5/1999 | Fujieda | 351/211 |

FOREIGN PATENT DOCUMENTS

| | | |
|---|---|---|
| 5-56931 | 3/1993 | Japan . |
| 10-14878 | 1/1998 | Japan . |
| 10-71122 | 3/1998 | Japan . |
| WO 92/14405 | 9/1992 | WIPO . |

*Primary Examiner*—George Manuel
*Attorney, Agent, or Firm*—Oliff & Berridge, PLC

[57] ABSTRACT

An ophthalmic apparatus including a measuring part for examining or measuring an eye to be examined by bringing the measuring part into predetermined alignment condition relative to the eye, the apparatus comprising a target projecting device for projecting a plurality of alignment targets on a cornea of the eye with predetermined arrangement therebetween, a luminance point detecting device for detecting luminance points of which intensity is equal to, or brighter than a predetermined intensity level from luminance points formed on the cornea of the eye upon projecting the alignment targets thereon by the target projecting device, an irregular luminance point detecting device for detecting irregular luminance points based on information about the luminance points detected by the luminance point detecting device and a movement instructing device for instructing movements of the measuring part relative to the eye based on the information about the luminance points from which the irregular luminance points detected by the irregular luminance point detecting device are excluded.

18 Claims, 11 Drawing Sheets

FIG. 13A
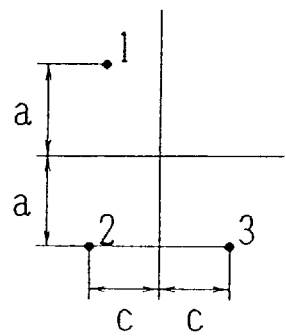 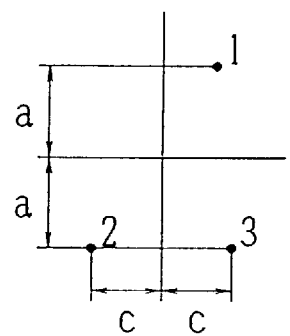
FIG. 13B
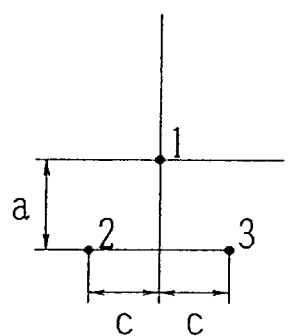
FIG. 13C
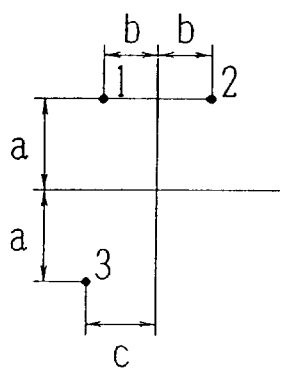 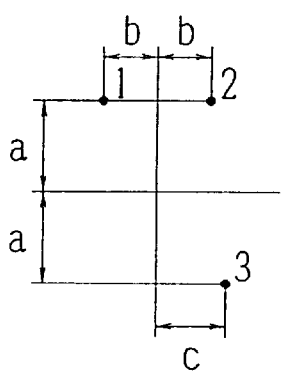
FIG. 13D
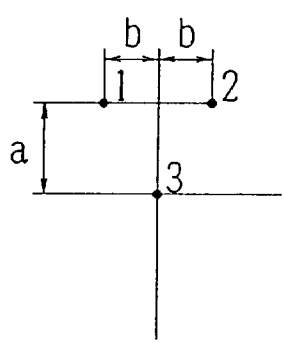
FIG. 13E
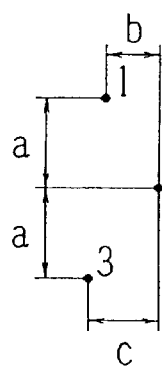 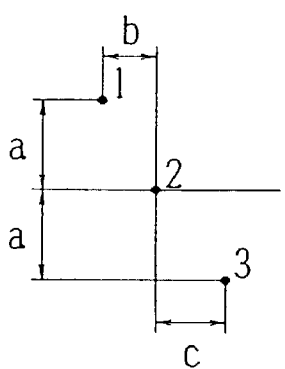 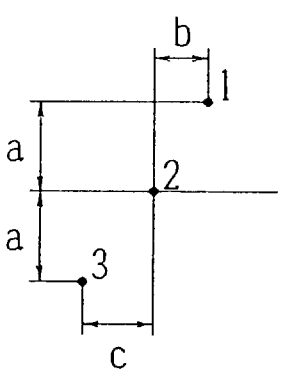 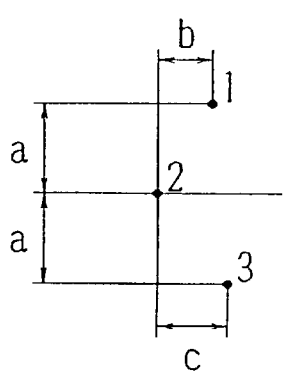

OPHTHALMIC APPARATUS

BACKGROUND OF THE INVENTION

1. Field of the Invention

The present invention relates to an ophthalmic apparatus, and more particularly, relates to an ophthalmic apparatus having a measuring part for examining and measuring an eye to be examined and moves the measuring part with respect to the eye to have a predetermined positional relationship therebetween.

2. Description of Related Art

An ophthalmic apparatus, such as an eye refractive power measuring apparatus or a noncontact type tonometer, measures an eye to be examined by moving a measuring optical system provided in the apparatus so as to make a predetermined alignment with respect to the eye. In one alignment mechanism which has been suggested, alignment target images formed by projecting alignment targets on a cornea of the eye are detected and based on information detected thereby, moving means for moving the apparatus is driven and controlled so as to automatically adjust or maintain the alignment. To drive and control the apparatus, the alignment target image being a luminance point is formed on a corneal vertex by projecting an alignment target light from the front of the eye, or a corneal center is detected based on a positional relationship among luminance points formed on the cornea by projecting a plurality of alignment target light thereto.

However, influenced by conditions of a corneal surface, light producing objects (a fluorescent and the like) and tears of an examinee, scattered light may appear as a lot of luminance points on the corneal surface. The luminance points may not be distinguished from alignment target images, which is likely to interfere with a corneal center detection. In such cases mentioned above, alignment conditions may be wrongly judged or may not be detected at all.

As for an alignment mechanism which stores information about luminance points in sequence, if many luminance points are detected due to scattered light, the detection may stop halfway though it because of exhaustion of available memory.

SUMMARY OF THE INVENTION

The present invention has been made in view of the above circumstances and has an object to overcome the above problems and to provide an ophthalmic apparatus which is capable of detecting alignment conditions easily by minimizing influence of scattered light.

Additional objects and advantages of the invention will be set forth in part in the description which follows and in part will be obvious from the description, or may be learned by practice of the invention. The objects arid advantages of the invention may be realized and attained by means of the instrumentalities and combinations particularly pointed out in the appended claims.

To achieve the objects and in accordance with the purpose of the present invention, as embodied and broadly described herein, an ophthalmic apparatus including a measuring part for examining or measuring an eye to be examined by bringing the measuring part into predetermined alignment condition relative to the eye, the apparatus comprises target projecting means for projecting a plurality of alignment targets on a cornea of the eye with predetermined arrangement therebetween, luminance points of which intensity is equal to, or brighter than a predetermined intensity level from luminance points formed on the cornea of the eye upon projecting the alignment targets thereon by the target projecting means, irregular luminance point detecting means for detecting irregular luminance points based on information about the luminance points detected by the luminance point detecting means and movement instructing means for instructing movements of the measuring part relative to the eye based on information about the luminance points from which the irregular luminance points detected by the irregular luminance point detecting means are excluded.

In another aspect of the present invention, an ophthalmic apparatus including a measuring part for examining or measuring an eye to be examined by bringing the measuring part into predetermined alignment condition relative to the eye, the apparatus comprises target projecting means for projecting a plurality of alignment targets on a cornea of the eye, luminance point detecting means for detecting luminance points of which intensity is equal to, or brighter than a predetermined intensity level from luminance points formed on the cornea of the eye upon projecting the alignment targets thereon by the target projecting means, calculating means for calculating positions of each luminance point when it is judged that the number of the luminance points detected by the luminance point detecting means is equal to, or less than a predetermined amount and target image locating means for locating positions of each alignment target image by distinguishing the luminance points of the alignment target images from the luminance points due to scattered light based on a result calculated by the calculating means.

According to the present invention, even in cases where many luminance points appear on the corneal surface due to scattered light, by not performing the detection with respect to the part where luminance points are dense, it will be easy to identify the alignment target images. Consequently, misjudgement of the alignment conditions can be reduced. In addition, available memory for storing information about the luminance points may be used more efficiently.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIGS. 13A–13E are views showing positional relationship among target images in the cases where three target images are detected;

DETAILED DESCRIPTION OF THE PREFERRED EMBODIMENTS

A detailed description of one preferred embodiment of an ophthalmic apparatus embodying the present invention will now be given referring to the accompanying drawings.

Hereinafter, a noncontact tonometer will be described as an apparatus of the preferred embodiment with reference to the accompanying drawings.

Overall Configuration

Figure 1:
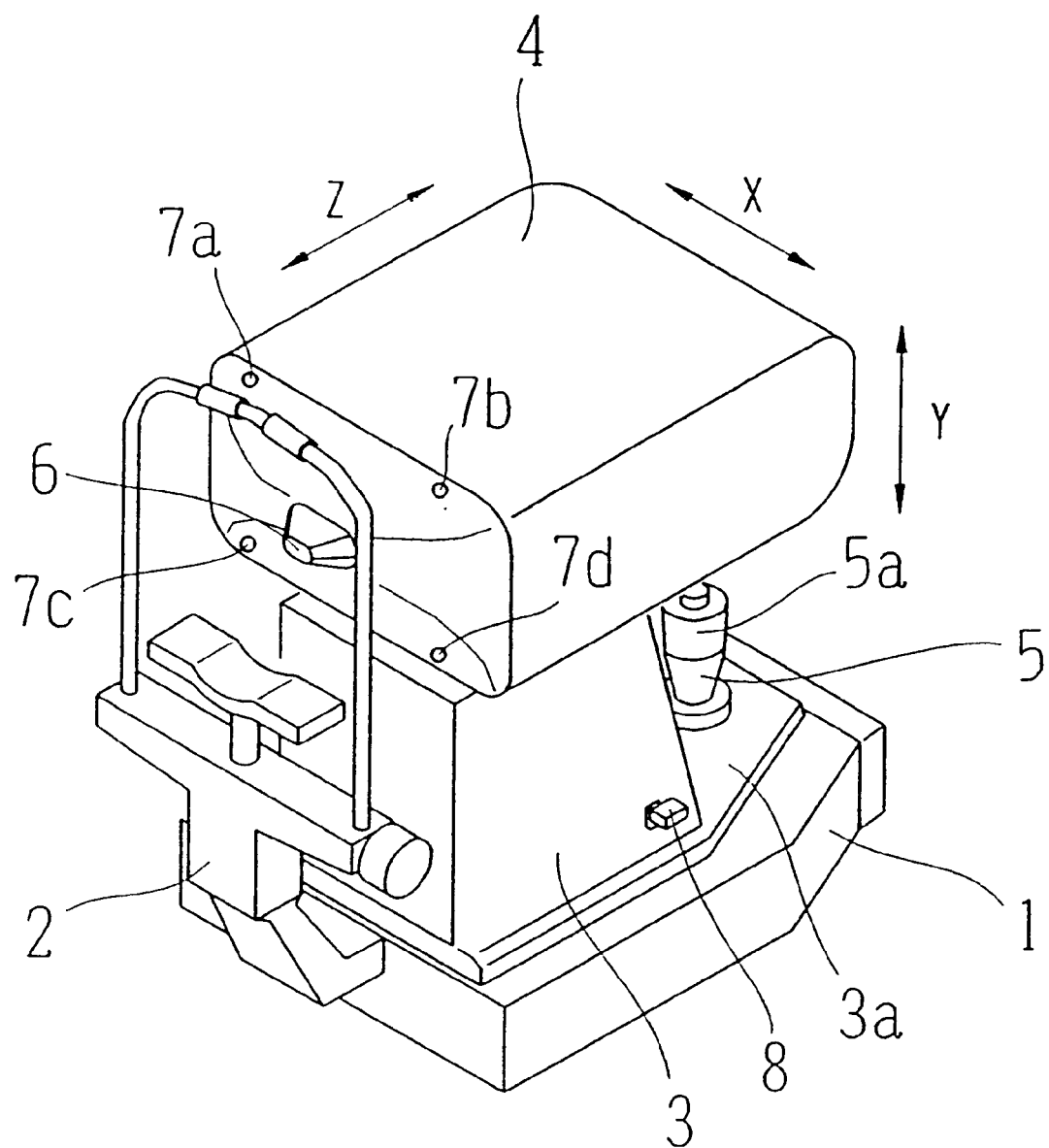
FIG. 1 is a schematic diagram showing an external representation of a noncontact tonometer of the preferred embodiment.

FIG. 1 is a schematic diagram showing an external representation of the noncontact tonometer of the preferred embodiment. Reference numeral 1 denotes a base to which a jaw stand 2 is fixed for fixing an eye E to be examined. 3 is a body part, 4 is a measuring part which stores an optical system mentioned below, and 5 is a joystick which is used in order to move the body part 3 and the measuring part 4. The body part 3 slides along a horizontal plane of the base 1 in a back-and-forth direction (Z-direction) and in a right-and-left direction (X-direction) by operating the joystick 5, and the measuring part 4 moves in a vertical direction (Y-direction) relative to the body part 3 by operating the joystick 5.

The noncontact tonometer is comprising a spherical part and a lower edge which are formed on a lower portion of a shaft of the joystick 5, a sliding plate on which the lower edge swings, a friction plate which touches the sliding plate and is attached to the base 1, and a spherical bearing inside a housing 3a which is united with the body part 3. This configuration allows to accomplish movements of the body part 3 in a horizontal direction relative to the base 1. In addition, a rotation knob 5a is disposed around the outer circumference of the joystick 5 and a slit plate rotates with the rotation knob 5a. A light source and a light-receiving element which are disposed having the slit plate therebetween detect a rotation direction and a rotation amount of the rotation knob 5a (the slit plate) from a signal transmitted from the light-receiving element. According to the detected rotation direction and the rotation amount, a Y-axis motor which moves the measuring part 4 in a vertical direction is driven and controlled, thereby moves the measuring part 4 in a vertical direction relative to the body part 3. For a detailed description of the joystick mechanism, see Japanese Patent Publication NO. HEI6 (1994)-7292 corresponding to U.S. Pat. No, 5,406,076 (title of the invention: JOYSTICK MECHANISM FOR OPHTHALMIC APPARATUS) by the applicant of the present invention.

The measuring part 4 also moves in a right-and-left direction (X-direction) as well as in a back-and-forth direction (Z-direction) relative to the body part 3. These movements are made not by the joystick 5, but by an X-axis motor and a Z-axis motor which are driven and controlled by a control circuit mentioned below.

6 is a nozzle part in which a nozzle for jetting compressed gas to the eye E is disposed. On the examinee side of the measuring part 4, the four light sources 7a–7d which project alignment targets on a periphery of a cornea Ec of the eye E are disposed with their center at the nozzle part 6. On a lateral side of the body part 3, a knob 8 is disposed in order to regulate limits of movement of the nozzle part 6 toward the eye E. On the side of joystick 5 of the body part 3 (the examiner side), a TV monitor is provided for use in observation.

Optical System

Figure 2:
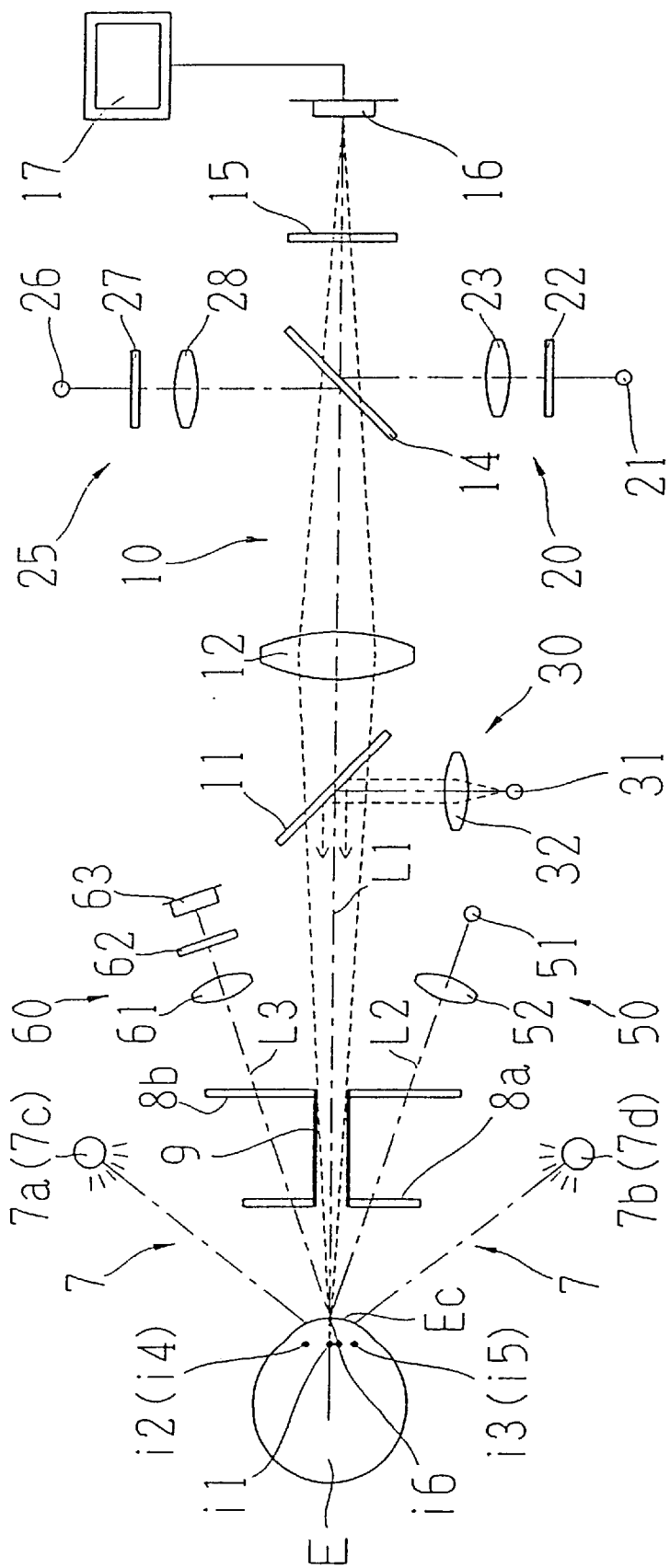
FIG. 2 is a block diagram showing an important part of an alignment optical system of the noncontact tonometer of the preferred embodiment.

FIG. 2 is a block diagram showing an important part of the alignment optical system of the apparatus as seen from the top. The noncontact tonometer alters the cornea Ec into a predetermined shape by jetting compressed gas thereto. Intraocular pressure of the eye is measured based on the gas pressure which is detected directly or indirectly. However, this measurement mechanism has little relationship with the present invention, therefore the description is omitted. For a detailed description, see Japanese Patent Publication No. HEI 5 (1993)-56931 corresponding to U.S. patent Ser. No. 08/351,583 which is a Continuation Application of U.S. patent Ser. No. 07/933,303 (title of the invention: NONCONTACT TYPE TONOMETER) by the applicant of the present invention.

Observation Optical System 10 is an observation optical system of which optical axis is denoted by L1. The observation optical system 10 also serves as a target detecting optical system for detecting first and second alignment targets for alignment in a vertical and a horizontal directions (mentioned below). On the optical path of the observation optical system 10, the nozzle 9 for jetting the gas to alter the corneal shape is disposed with being held by glass plates 8a and 8b and the axis thereof coincides with the optical axis L1. On the optical axis L1, a beam splitter 11, an objective lens 12, a beam splitter 14, a filter 15, and a CCD camera 16 are disposed. The filter 15 has such characteristics that it transmits the light bundles (wavelength 950 nm) of the first and second alignment target optical systems (mentioned below) and a light bundle (wavelength 950 nm) of a reticle projecting optical system (mentioned below), but does not transmit visible light and a light bundle (wavelength 800 nm) of a distance target projecting optical system (mentioned below). Therefore, unnecessary noise light is prevented from reaching the CCD camera 16. An image of an anterior part of the eye E and target images photographed by the CCD camera 16 are displayed onto the TV monitor 17, and the examiner observes the images.

Reticle Projecting Optical System 20 denotes the reticle projecting optical system. 21 is a reticle projecting light source which emits the infrared light having wavelength of 950 nm, 22 is a reticle plate on which a circle-shaped mark is formed, and 23 is a projecting lens. The reticle on the reticle plate 22 is illuminated by the reticle projecting light source 21 and is photographed by the CCD camera 16 through the projecting lens 23 the beam splitter 14 and the filter 15.

In order to facilitate the detection of the target images by the CCD camera 16, the light bundle emitted from the reticle projecting light source 21 is modulated with a predetermined frequency, so that the light bundle from the reticle projecting light source 21 is distinguished from light bundles emitted from the light sources 7a–7d and a light source 31. To make a reticle image easily observed on the TV monitor 17, it is also possible to adjust the light amount so as to distinguish the reticle image from the target images based on the differences in intensity, or the reticle image may be generated by a pattern generator electrically.

Eye Fixation Optical System

An eye-fixation optical system 25 includes a light source 26 which emits visible light, an eye-fixation plate 27 and a projecting lens 28. When the light source 26 is turned on, a light bundle emerged from the eye-fixation plate 27. The light bundle passes through the nozzle 9 via the projecting lens 28, the beam splitter 14, the objective lens 12, the beam splitter 11 and then enters the eye E.

The First Alignment Target Projecting Optical System

30 denotes the first alignment target projecting optical system. 31 is the central target-projecting light source, and 32 is a projecting lens. The light source 31 emits the infrared light having wavelength of 950 nm. The infrared light bundle emitted from the light source 31 is made to be a parallel light bundle by passing through the projecting lens 32, and then reflected by the beam splitter 11. Thereafter, the light bundle goes through the nozzle 9 along the optical axis L1 so as to irradiate the cornea Ec. The light bundle reflected from the cornea Ec by mirror reflection forms the first alignment target i1 which is a virtual image of the light source 31. The light bundle of the first alignment target i1 forms the image of the first alignment target i1 on a photographing element of the CCD camera 16.

(The Second Alignment Target Projecting Optical System)

The second alignment target projecting optical system 7 includes four light sources 7a–7d (see FIG. 1). The light sources 7a and 7b are disposed at the same height from the optical axis L1 and so are 7c and 7d. That is say the optical distance from each light source is made to be the same. The light sources 7a–7d emit infrared light having the same wavelength of 950 nm that the light source 31 of the first alignment target projecting optical system 30 emits. The light emitted from the light sources 7a and 7b irradiates the periphery of the cornea Ec from an oblique-upper direction, thereby forms targets i2 and i3 which are virtual images of the light sources 7a and 7b respectively. The light sources 7a and 7b are also used for detecting opening conditions of an eyelid. The light transmitted from the light sources 7c and 7d irradiates the periphery of the cornea Ec from an oblique-lower direction, thereby forms targets i4 and is which are virtual images of the light sources 7c and 7d respectively. The light sources 7a–7d are also used as illumination light sources for illuminating the anterior part of the eye E.

The light bundles of four targets i2, i3, i4, and i5 enter the CCD camera 16 via the observation optical system 10 and form the images on the photographing element of the CCD camera 16.

The Distance Target Projecting Optical System

50 is the distance target projecting optical system of which optical axis is denoted by L2. The optical axis L2 is arranged inclined to the optical axis L1, and the two optical axes intersect with each other at a point which is a predetermined working distance away from the nozzle 9. 51 is a light source for projecting a distance target, which emits light having wavelength of 800 nm which is different from that of the light sources 7a–7d and the light source 31. 52 is a projecting lens.

The light emitted from the light source 51 is made to be a parallel light bundle by passing through the projecting lens 52, and then irradiates the cornea Ec along the optical axis L2. The light bundle reflected from the cornea Ec by mirror reflection forms a target i6 which is a virtual image of the light source 51.

The Distance Target Detecting Optical System

60 is a distance target detecting optical system of which optical axis is denoted by L3. The optical axis L3 and the optical axis L2 are symmetrical with respect to the optical axis L1, and the two optical axes intersect with each other at a point on the optical axis L1. Disposed on the optical axis L3 are a photo receiving lens 61, a filter 62 and a one-dimensional detecting element 63. The filter 62 has such characteristics that it transmits the light bundle having wavelength of 800 nm emitted from the light source 51, but does not transmit the light bundles having wavelength of 950 nm emitted from the light sources 7a–7d and the light source 31. Therefore, noise light is prevented from reaching the one-dimensional detecting element 63.

The light forming the target i6, which is emitted from the light source 51 and reflected from the cornea Ec, enters the one-dimensional detecting element 63 via the photo receiving lens 61 and the filter 62. As the eye E moves toward the observation optical axis L1 (in a back-and-forth direction), the image of the target i6 also moves in a direction of the one-dimensional detecting element 63. The position of the eye E, therefore, is detected from the deviation of the image of the target i6 on the one-dimensional detecting element 63.

The Control System

Figure 3:
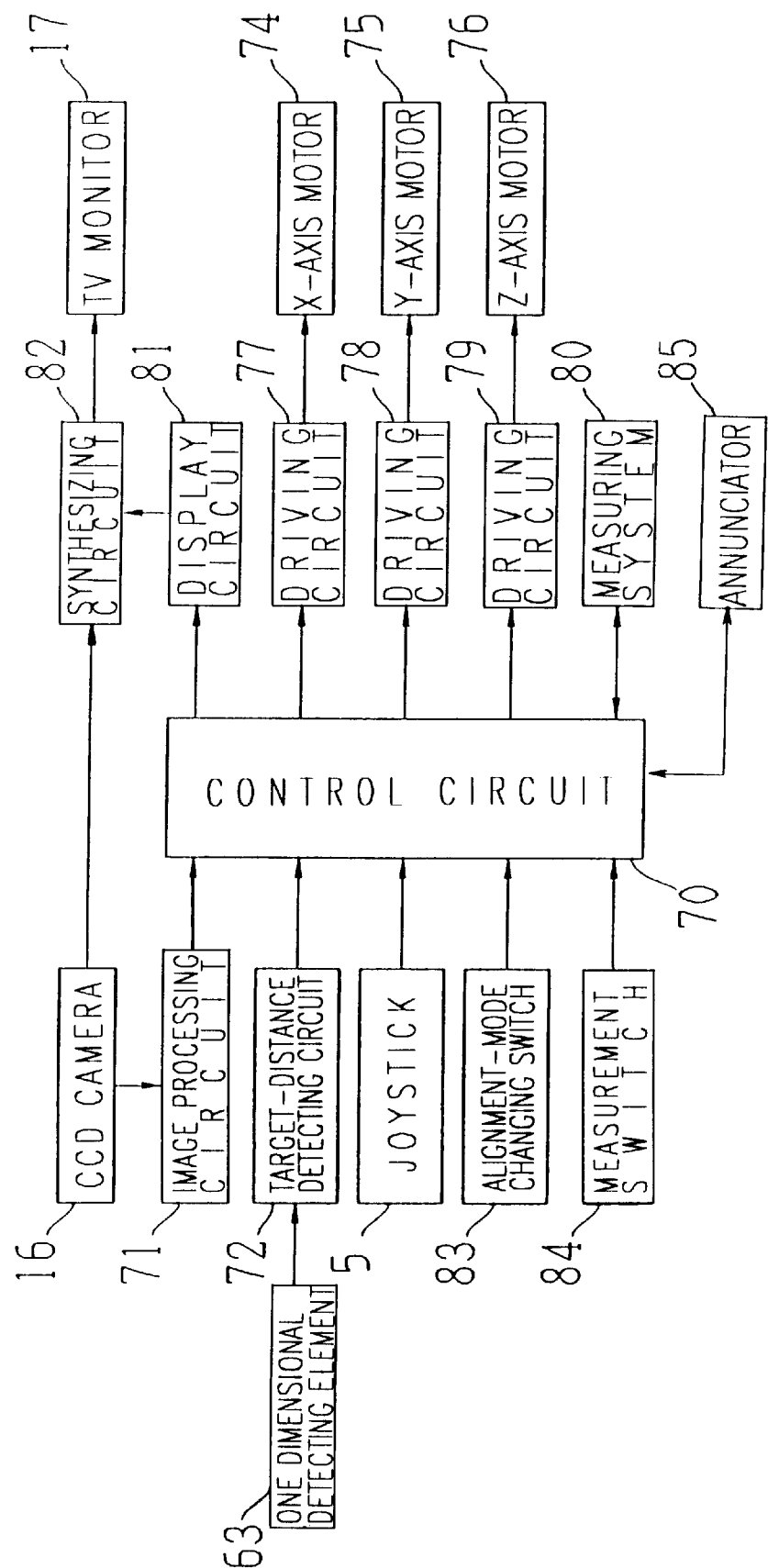
FIG. 3 is a block diagram showing an important part of a control system of the noncontact tonometer of the preferred embodiment.

FIG. 3 shows an important part of a control system of the apparatus. 70 is a control circuit, 71 is an image processing circuit, and 72 is a target-distance detecting circuit. 74–76 are the X-axis motor, the Y-axis motor and the Z-axis motor respectively, each of which drives the measuring part 4 relative to the body part 3. 77–79 are driving circuits for the respective motors. 80 is a measuring system, 81 is a display circuit which generates character information and figures and the like, and 82 is a synthesizing circuit. 83 is an alignment-mode changing switch for selecting either an auto alignment performed by the apparatus based on the target detection or a manual alignment performed only by the examiner with operating the joystick 5. 84 is a measurement switch for inputting a measurement starting signal.

The image processing circuit 71 gives an image processing to the photographed image transmitted from the CCD camera 16, and inputs the processed result to the control circuit 70. The control circuit 70 obtains the positional information of the target images and a pupil.

The control circuit 70 also obtains the deviation information from the eye E in a back-and-forth direction based on the signal transmitted from the one-dimensional detecting element 63 via the target-distance detecting circuit 72. The control circuit 70 sends the deviation information obtained thereby to the display circuit 81, then the display circuit 81 generates a graphic signal of a distance mark and a position signal indicating a position on the TV monitor 17 based on the deviation information. The output signals from the display circuit 81 are synthesized with a picture signal from the CCD camera 16 in the synthesizing circuit 82, then sent to the TV monitor 17 and displayed thereon.

Figure 4:
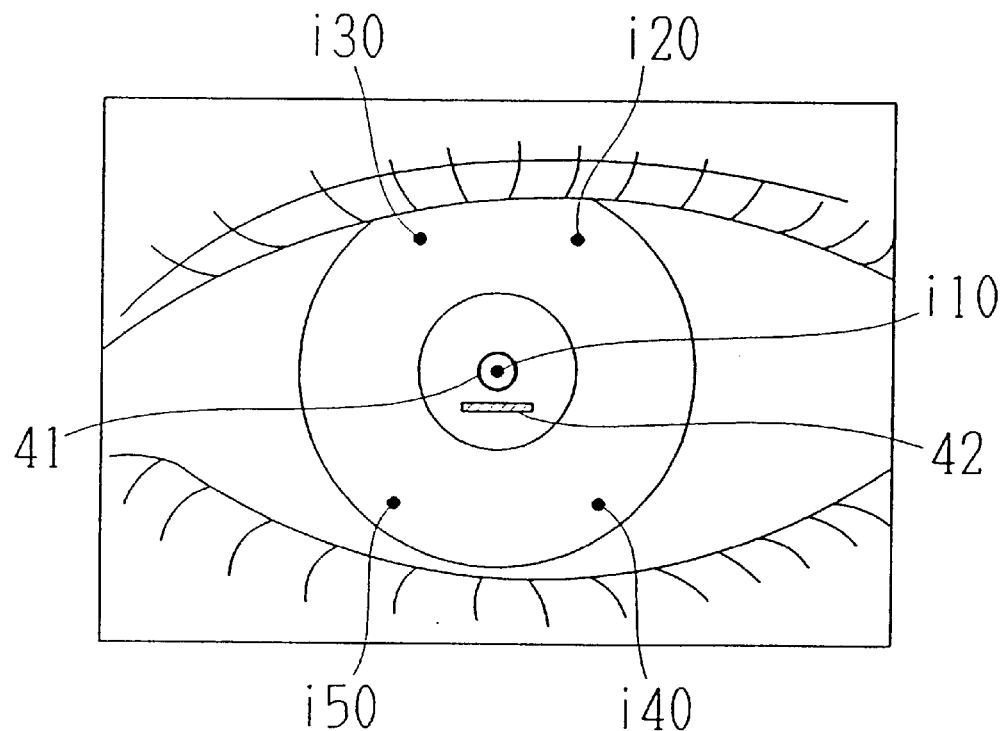
FIG. 4 is a view showing an example of a screen displayed on a TV monitor under conditions where the eye is in proper alignment.

FIG. 4 is a view showing an example of a screen displayed on the TV monitor 17 under conditions where the alignment in X, Y-directions is made properly. Under the conditions where the alignment in X, Y-directions is appropriate, the four target images i20, i30, i40 and i50 which are formed by the second alignment target projecting optical system 7 on the periphery of the cornea Ec and the target image i10 which is formed by the first alignment target projecting optical system 30 in the vicinity of the corneal center are displayed. 41 denotes the reticle image. 42 denotes the distance mark which moves vertically on the reticle image 41 in real time corresponding to the distance between the cornea Ec and the nozzle part 6. When the cornea Ec is at an appropriate working distance, the distance mark 42 will be superimposed on the reticle image 41.

The operations of the apparatus having above-described configuration will be described hereinafter. The examiner fixes the eye E with the use of t he jaw stand 2, and makes the eye E fix on the fixation target. When preparations for the measurement are done, the examiner operates the joystick 5 with observing the TV monitor 17, thereby roughly aligns the measuring part 4 with the eye E until the anterior part of the eye and the alignment targets appear on the TV monitor 17.

Once it becomes ready to detect the alignment targets from the picture signal transmitted from the CCD camera 16, the control circuit 70 drives and controls the X-axis motor 74 and the Y-axis motor 75 so as to bring the measuring part 4 in a completed alignment in X, Y-directions.

Next, the process to detect luminance points of the alignment target images (referred to simply as the "target images" hereinafter) from the output signal from the CCD camera 16 will be described hereinafter (see FIG. 6, the flow chart). Once the picture signal carrying one screen data is stored into image memory of the image processing circuit 71, the luminance point detection is carried out. The luminance point detection is started from the point having the coordinates of (X, Y) =(0, 0) at an upper-left corner of the screen (STEP-1-STEP-3) and then toward the point having the coordinates of (X, Y) =(Xlim, Ylim) at a lower-right corner of the screen (STEP-9-STEP-12). During the detection, if a luminance signal which is equal to or exceeds a predetermined threshold is detected (STEP-4), the luminance point edge, which is a signal indicative of a position of the rising edge, is counted (even without storing all the positions of the luminance signals, the approximate Y coordinates of each luminance point can be found from the rising signals). If the number of luminance point edges is within a predetermined storage capacity (less than 100, for example), the coordinates are stored (STEP-5–STEP-8).

In the detection of the luminance point edges as described above, if the number of edges is within the predetermined storage capacity and yet the detection is completed all the way through the coordinates (X, Y)=(Xlim, Ylim) (STEP-11), the positions of each luminance point are calculated from the positional information about the luminance point edges stored in data memory. Each luminance point has a different dimension, however, the individual position can be calculated, regardless of the difference in size, by seeking the center of the continuous luminance point edges along the Y coordinate (STEP-13).

Once the individual positions of the luminance points are calculated, luminance points due to the scattered light and the luminance points of the target images are distinguished, and thereby locate the alignment target images (STEP-14).

Figure 5:
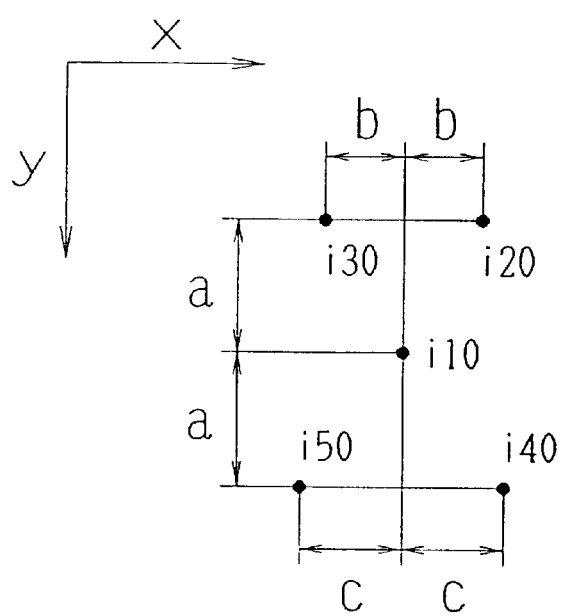
FIG. 5 is a view showing positional relationship among five target images based on which alignment conditions are judged.

Hereinafter, how to distinguish the alignment target images will be described. First of all, the positional relationship among five target images which functions as a criterion for distinguishing the target images will be described with reference to FIG. 5. FIG. 5 is a view showing the positional relationship among the target images formed by the respective alignment light under conditions where the alignment is made properly with the eye E having a certain corneal curvature. Let i10 denote the first alignment target image under the proper alignment. The target images i40 and i50 are at positions where approximately a width of a away from i10 in a downward direction along the Y-axis and a width of c away from i10 in an opposite direction along the X-axis. The target images i20 and i30 are at positions where approximately the width of a away from i10 in an upward direction along the Y-axis and a width of b away from i10 in a opposite direction along the X-axis. The width of b has to be narrower than the width of c (and yet wider than the half of it). These positional relationship and intervals vary to some extent, but not greatly, corresponding to the corneal shape and the relative position of the apparatus with respect to the eye E. Therefore, by comparison of the positional relationship and intervals with the positional information about the luminance points, the luminance points of the target images are distinguished from the luminance points due to the scattered light. In addition, the target images forming each of the luminance point are identified as well.

Figure 7:
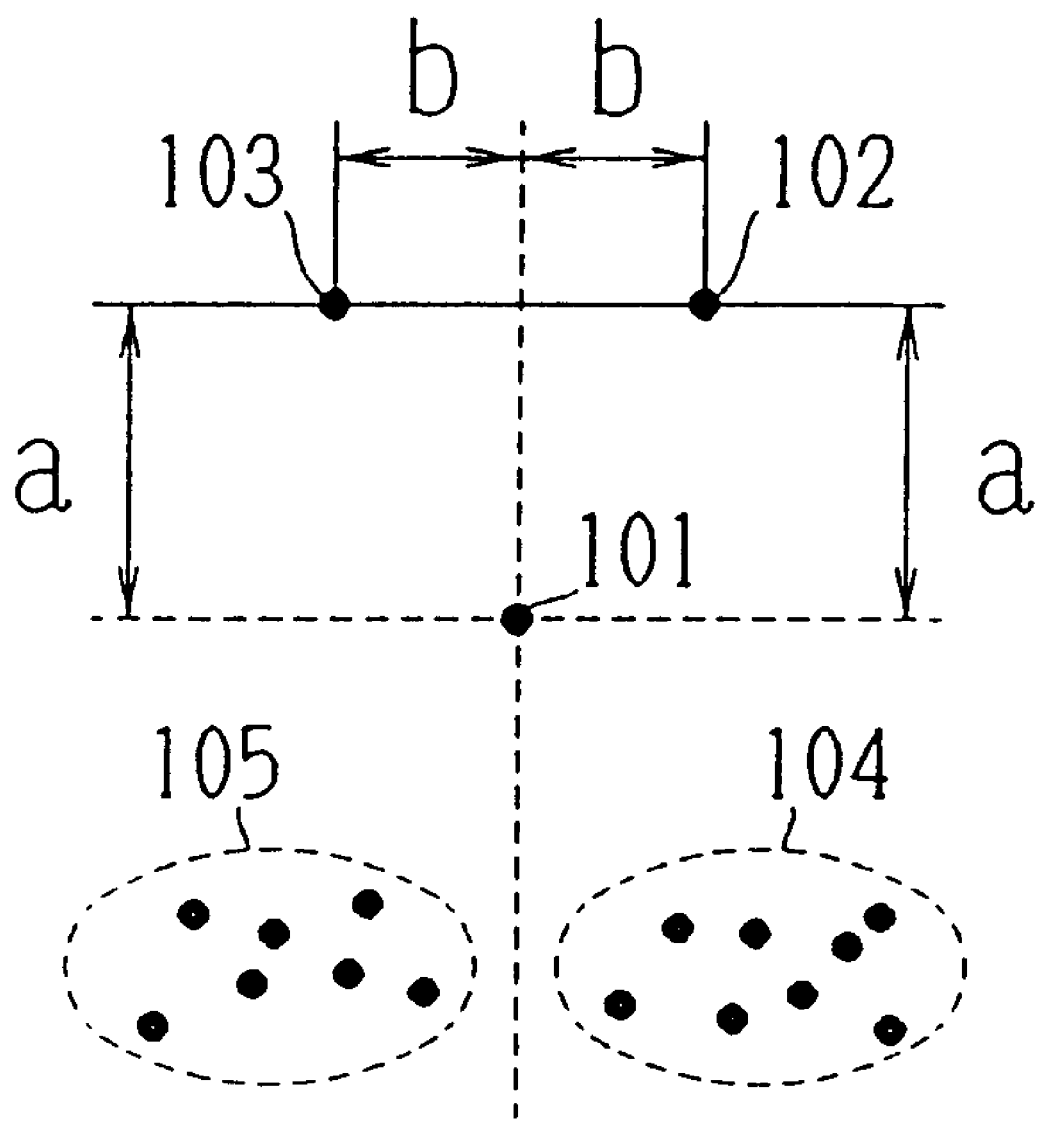
FIG. 7 is a view illustrating a way to distinguish target images from luminance points forming groups.

Suppose, for examples, separate luminance points 101–103 and many luminance points forming groups of 104 and 105 are detected as shown in FIG. 7. The groups of luminance points 104 and 105 are the luminance points due to the scattered light caused under the influence of tears of the examinee or the like. The positional relationship of each luminance point and the distance thereamong are compared with the criterion shown in FIG. 5, thereby delete the luminance points which are not likely to be the target images one by one. In the example shown in FIG. 7, the luminance points 101–103 can be identified as the target images i10, i20 and i30 respectively. The groups of luminance points 104 and 105 may include the target images i40 and i50. However, not being identified as the target images, they should not be included in the alignment information.

Once the target images are identified, the control circuit 70 moves and controls the measuring part 4 based on the number and the position of the target images so as to align the measuring part 4 with the eye (STEP-15). The operations of this alignment will be fully described later.

Figure 6:
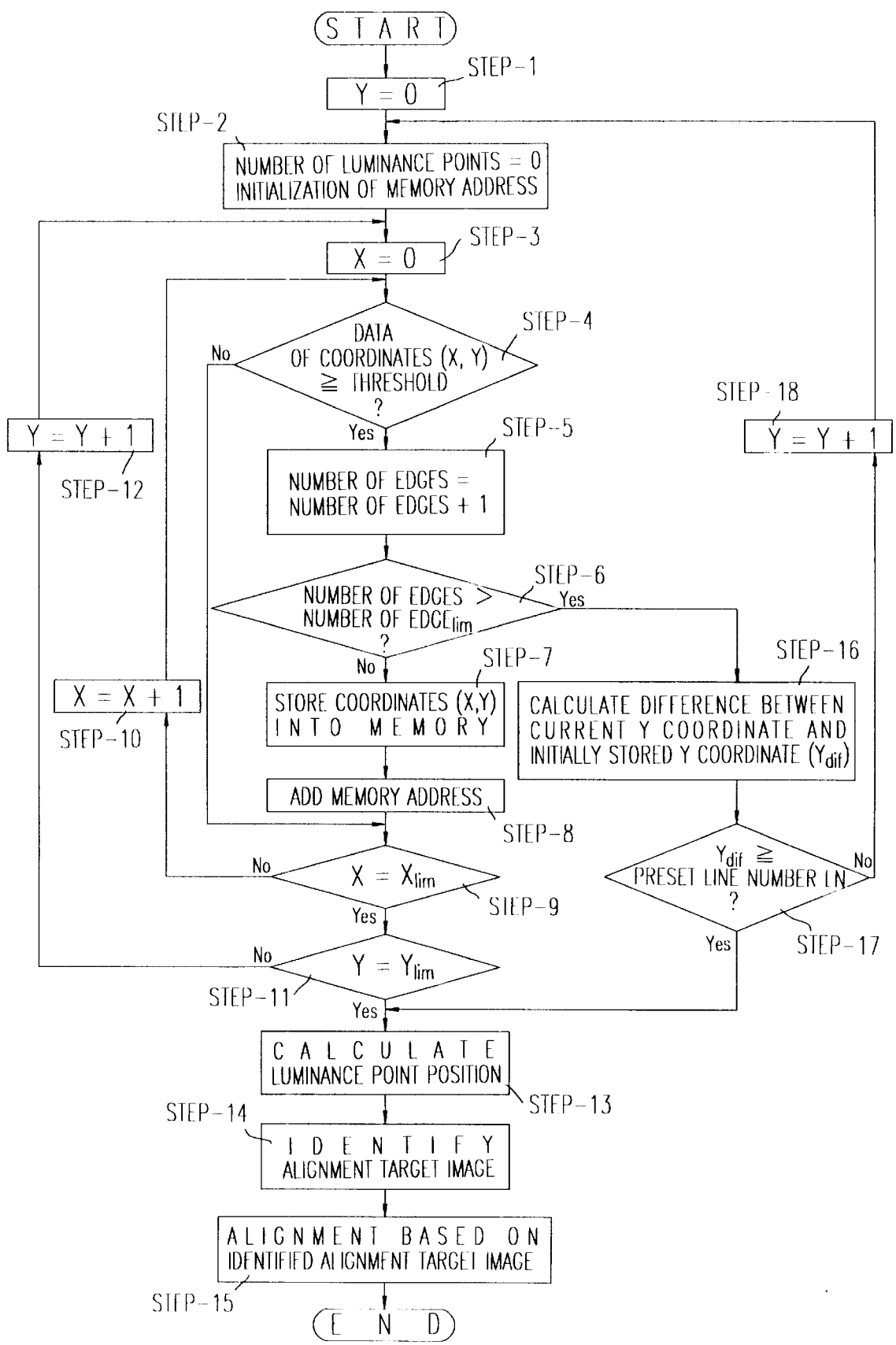
FIG. 6 is a flow chart showing a target image detecting process of the apparatus.

Here, a description is made regarding the cases where the number of luminance point edges stored in the data memory exceeds the predetermined storage capacity upon STEP-6 in FIG. 6. In these cases, the locative distribution of the luminance point edges will be the important factor. The locative distribution of the luminance point edges can be calculated from how many number of lines of the Y coordinates there are from the first detected luminance point edges (STEP-16). If the number of lines is within the preset number (hereinafter, referred to as the "preset line number LN"), the Y coordinate for the luminance point detection is updated to y+1 at the point where the number of luminance point edges exceeds the predetermined storage capacity (STEP-18), arid then goes back to the STEP-2 and initialize the number of luminance point edges and the coordinates stored in the data memory. Thereafter, STEP-3-STEP-12 are repeated again. Upon these STEPs, the coordinates of the luminance point edges will be overwritten, thereby the data indicative of the range defined by the preset line number LN will be erased from the data memory sequentially.

It should be noted here that the preset line number LN should be set so as to cover a range slightly wider than a range in which the target images i10, i20 and i30 or the target images i10, i40 and i50 can be detected (in consideration of individual difference). This is because upon identifying at least three target images, the measuring part 4 can be guided despite the luminance points due to the scattered light based on the number of target images and the positional relationship, which will be described later. If the scattered light appears on the surface of the cornea Ec due to a fluorescent and the like, for example, luminance points may appear densely in the upper part of the eye E. In these cases, data of the luminance point edges will exceed the predetermined storage capacity, but the distribution of the luminance points fall short of the preset line number LN because of the densely gathered luminance points. Therefore, the data corresponding to the gathered luminance points will be erased and the target images detected only in an area below the preset line number LN are subjected to the further detection.

On the contrary, the line number counted from the first detected luminance point edge exceeds the preset line number LN, the detection on the screen in process will be completed at this stage. Based on the information about the luminance point edges stored into the data memory at this point (information about the movement amount may be added), respective luminance points will be located and the corresponding target images are identified, and thereby performs alignment (STEP-13–STEP-15). In an example shown in the FIG. 7, if the groups of luminance points 104 and 105 contain many luminance points, the storage capacity of the memory is used up halfway through the detection. The line number of the Y-axis exceeds the preset line number LN, therefore the luminance points within the range up to this point will be located and corresponding target images are identified.

In the embodiment which has been described above, the number of luminance point edges is counted and whether it has reached the predetermined storage capacity is judged. However, it is also possible, as is done in STEP-13, to suppose that each luminance point has areas, so that judgements in STEP-16 and after can be made based on the number of areas and the distribution.

If no valid luminance points (or information about the luminance points) are obtained after eliminating irregular luminance points, an annunciator 85 produces a beep or the like to alert the examiner. In this case, the examiner starts over the operation again.

<In the cases where one target image is detected among five in all>

Only in the cases where the detected target image is identified as the target image i10, the measuring part 4 is made to move. If not, the measuring part 4 is made not to move. When the detected target image satisfies both of the following requirements, the detected target image is identified as the target image i10.

I. The detected target image is within a predetermined range (for example, within a size corresponding to the diameter of the nozzle 9) with a standard position at its center.

II. The deviation of Z-direction relative to the appropriate working distance is within a predetermined range (the image of the target i6 formed by the distance target projecting optical system 50 can be detected by the one-dimensional detecting element 63 and the deviation thereof is within the predetermined range)

<In the cases where two target images are detected among five in all>

Figure 8A:
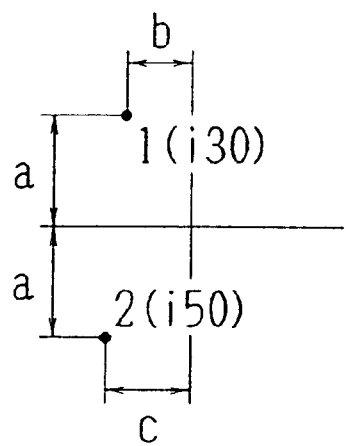
FIGS. 8A and 8B are views showing a first combination to identify corresponding target images in the cases where two target images are detected.
Figure 8B:
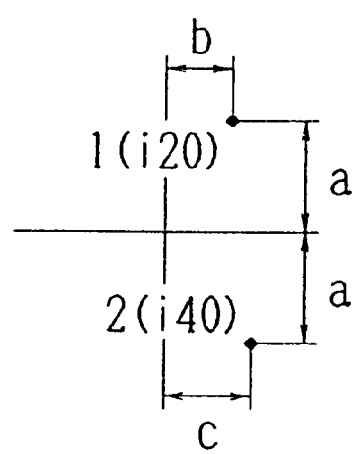

[A] In the cases where the difference between the X coordinate of the first target image and that of the second target image is small (equal to, or less than the width of b) and the difference between the Y coordinate of the first target image and that of the second target image is large (approximately equal to the width of 2a): As shown in FIGS. 8A and 8B, there are two possible combinations, one is the combination of the target images i30 and i50, and the other is the combination of the target images i20 and i40. These two combinations are distinguished from each other as follows.

I. If the following condition is satisfied, the detected target images can be identified as i30 and i50; the X coordinate of the first target image>the X coordinate of the second target image.

II. If the following condition is satisfied, the detected target images can be identified as i20 and i40;

the X coordinate of the first target image<the X coordinate of the second target image.

Figure 9A:
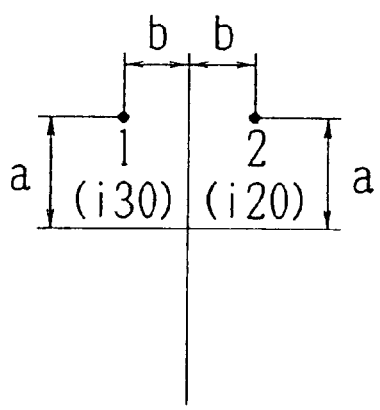
FIGS. 9A and 9B are views showing a second combination to identify corresponding target images in the cases where two target images are detected.
Figure 9B:
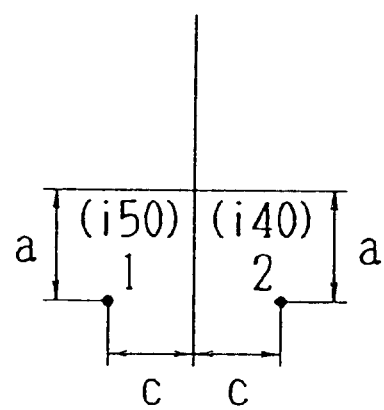

[B] In the cases where the Y coordinate of the first target image and that of the second target image is approximately the same: As shown in FIGS. 9A and 9B, there are two possible combinations, one is the combination of the target images i20 and i30 and the other is the combination of the target images i40 and i50. These two combinations are distinguished from each other as follows.

I. If the following condition is satisfied, the detected target images can be identified as i20 and i30;

the difference between the X coordinate of the first one and that of the second target image≦the width of 2 b.

II. If the following condition is satisfied, the target images can be identified as i40 and i50;

the difference between the X coordinate of the first target image and that of the second target image>the width of 2 b.

Figure 10A:
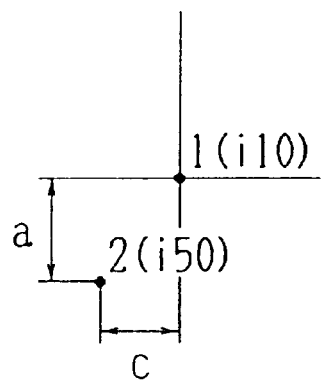
FIGS. 10A and 10B are views showing a third combination to identify corresponding target images in the cases where two target images are detected.
Figure 10B:
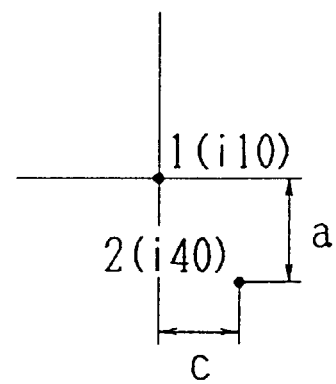

[C] In the cases where the difference between the Y coordinate of the first target image and that of the second target image is approximately the width of a and only the first target image is within the predetermined range having the standard position (center optical axis) as its center: As shown in FIGS. 10A and 10B, there are two possible combinations, one is the combination of the target images i10 and i40 and the other is the combination of the target images i10 and i50. In either case, the first one is identified as the target image i10.

Figure 11A:
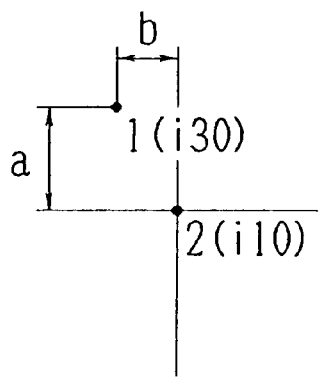
FIGS. 11A and 11B are views showing a fourth combination to identify corresponding target images in the cases where two target images are detected.
Figure 11B:
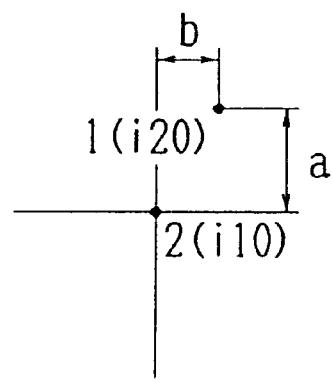

[D] In the cases where the difference between the Y coordinate of the first target image and that of the second target image is approximately the width of a and only the second target image is within the predetermined range having the standard position (center optical axis) as its center: As shown in FIGS. 11A and 11B, there are two possible combinations, one is the combination of the target images i10 and i20 and the other is the combination of the target images i10 and i30. In either case, the second one is identified as the target image i10.

Figure 12A:
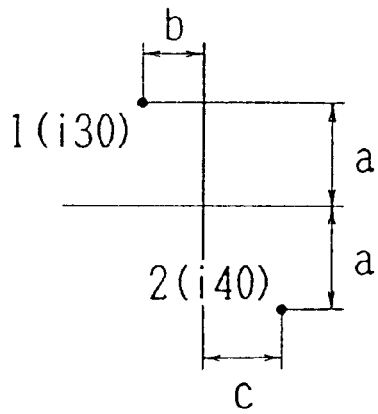
FIGS. 12A and 12B are views showing a fifth combination to identify corresponding target images in the cases where two target images are detected.
Figure 12B:
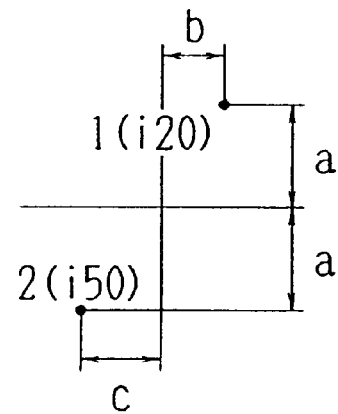

[E] In the cases where the X coordinate of the first target image and that of the second target image is not approximately the same, and the difference between the Y coordinate of the first target image and that of the second target image is large (approximately the width 2a): As shown in FIGS. 12A and 12B, there are two possible combinations, one is the combination of the target images i20 and i50 and the other is the combination of the target images i30 and i40.

Described hereinafter is the guidance method of the measuring part 4 based on the patterns of the target images identified in the aforementioned way and the positional relationship thereof. Firstly, in the patterns [C] and [D] mentioned above where the target image i10 can be identified, the measuring part 4 is guided based on the target image i10.

In the patterns where the target image i10 cannot be identified, the X, Y coordinates of the corneal center is calculated from the two target images, then the measuring part 4 is guided based on the obtained coordinates. For example, when the target images i30 and i50 are identified as is in the above-mentioned pattern [A] I., the Y coordinate of the corneal center is given by the expression [(Y1+Y2)/2]. On the other hand, regarding the target image i30 as the standard, the X coordinate is given by adding the width of b to X1 which is the X coordinate of i30 or by the expression [X1+b]. However, the X coordinate obtained in this way tends to be inaccurate due to the individual difference in the corneal size. Here, it should be noted that the coordinates of each target image generally vary in proportion to change in the corneal curvature. Utilizing this proportional relationship, in stead of the width of b, the product obtained by multiplying the Y-coordinates interval between the target images i30 and i50 by a constant α is added to the X1, which is the X coordinate of the target image i30 (or to the X2, which is the X coordinate of the target image i50). That is to say, the X coordinate in this case is given by the expression [X1+(Y2−Y1)×α]. This calculation allows to obtain the coordinates of the corneal center with higher accuracy compared to the coordinates obtained by simply adding the constant. The constant α is determined in advance by the arrangement relationship between the target projecting system and the target detecting system.

Likewise, when the target images i20 and i40 are identified as is in the pattern [A] II, the X, Y coordinates of the corneal center at the time are expressed a., ((X1−(Y2−Y1)×α, (Y1+Y2)/2)).

Also, based on the same concept, when the target images i20 and i30 are identified as is in the above-mentioned pattern [B] I, the X, Y coordinates of the corneal center at the time are expressed as ((X1+X2)/2, Y1+(|X1−X2|)×β). When the target images i40 and i50 are identified as is in the pattern [B] II, the X, Y coordinates of the corneal center at the time are expressed as (((X1+X2)/2, Y1−(|X1−X2|)×γ). Where the constants β and γ are also determined in advance by the arrangement relationship between the target projecting system and the target detecting system.

When the combination of target images i20 and i50 and the combination of target images i30 and i40 are identified as is in the above-mentioned pattern [E], the X, Y coordinates of the corneal center at the time are expressed as ((X1+X2)/2, (Y1+Y2)/2).

As has been described above, even if only two target images are detected, by guiding the measuring part 4 with reference to i10 if it is identified or with reference to the corneal center calculated from two target images if i10 can not be identified, the measuring part 4 always comes to move so that the center axis thereof coincides with the corneal center. Thereby, the guidance of the measuring part 4 becomes stable.

<In the cases where three target images are detected among five in all>

Once three or more target images are detected, with reference to the positional relationship thereamong, the target images i10 to i50 can be identified. The control circuit 70 obtains the X, Y coordinates (X1, Y1), (X2, Y2) and (X3, Y3) of respectively, the first target image, the second target image and the third target image, thereby moves the measuring part 4 in the following way.

[A] In the cases where the difference between the Y coordinate of the first target image and that of the second target image is approximately the width of 2a (and the Y coordinate of the second target image and that of the third target image are approximately the same): There are two possible patterns shown in FIG. 13A. These are the cases where the target image i10 is not detected, however, the control circuit 70 moves the measuring part 4 with assuming the corneal center is at the X, Y coordinates ((X2+X3)/2, (Y1+Y2)/2).

[B] In the cases where the difference between the Y coordinate of the first target image and that of the second target image is approximately the width of a and the Y coordinate of the second target image and that of the third target image are approximately the same: This is the pattern shown in FIG. 13B. The first target image is identified as the target image i10 so as to move the measuring part 4 with reference to the target image i10.

[C] In the cases where the Y coordinate of the first target image and that of the second target image are approximately the same and the difference between the Y coordinate of the second target image and that of the third target image is approximately the width of 2a: There are two possible patterns shown in FIG. 13C. As is in the pattern shown in FIG. 13A, the target image i10 is not detected, however, the control circuit 70 moves the measuring part 4 with assuming the corneal center is at the X, Y coordinates ((X1+X2)/2, (Y1+Y3)/2).

[D] In the cases where the difference between the Y coordinate of the second target image and that of the third target image is approximately the width of a and the Y coordinate of the first target image and that of the second target image are approximately the same: This is the pattern shown in FIG. 13D. The third target image is identified as the target image i10, thereby moves and controls the measuring part 4 with reference to the target image i10.

[E] In the cases where any of the above requirements are not satisfied: There are four possible patterns shown in FIG. 13E. In these patterns, the second target image is identified as the target image i10, thereby the measuring part 4 is made to move with reference to the target image i10.

<In the cases where the target image are four from among five in all>

The control circuit 70 obtains the X, Y coordinates of each target image, and moves the measuring part 4 in the following manner.

Figure 14A:
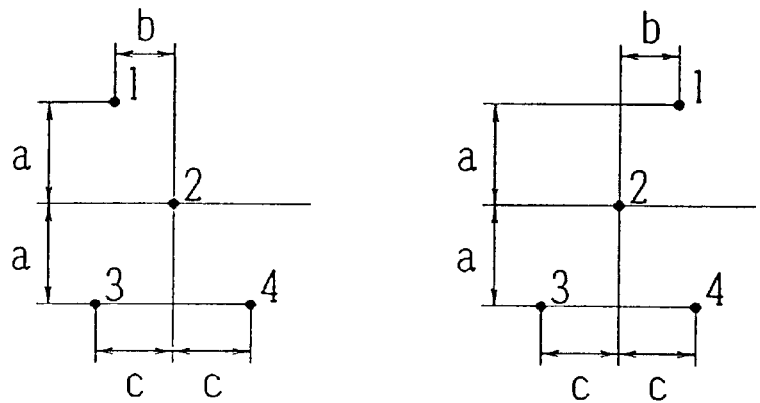
FIGS. 14A–14D are views showing positional relationship among target images in the case, where four or five target images are detected.

[A] In the cases where the Y coordinate of the first target image and that of the second target image are not approximately the same: There are two possible patterns shown in FIG. 14A. The second target image is identified as the target image i10, thereby moves the measuring part 4 with reference to the target image i10.

Figure 14B:
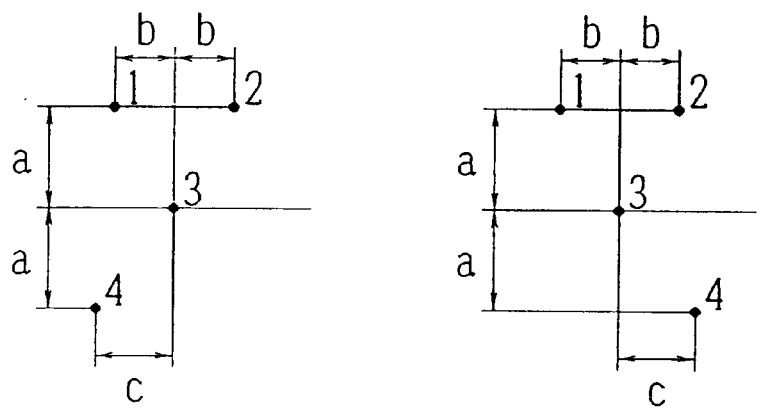

[B] In the cases where the Y coordinate of the third target image and that of the fourth target image are not approximately the same: There are two possible patterns shown in FIG. 14B. The third target image is identified as the target image i10, thereby moves the measuring part 4 with reference to the target image i10.

Figure 14C:
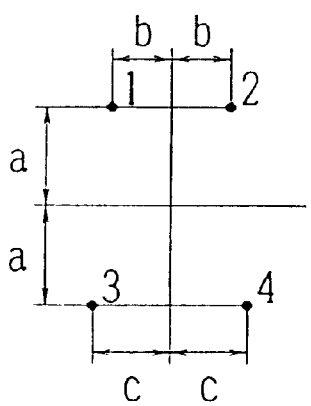
Figure 14D:
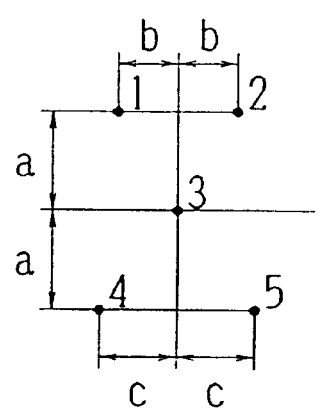

[C] In the cases other than above-mentioned patterns A and B: The pattern is shown in FIG. 14C. In this pattern, only the target image i10 is not detected, therefore the measuring part 4 is moved with assuming that the corneal vertex is at the midpoint of the four target images, for example at the coordinates of ((X1+X2)/2, (Y1+Y3)/2).

<In the cases where the target image are five from among five all>

All target images are detected, therefore the target image i10 is as well identified. The measuring part 4 is made to move with reference to the target image i10.

How to guide the measuring part 4 based on the number and the positions of detected target images has been described (it is practically the same as the invention disclosed in Japanese Patent Publication No. HEI 10 (1998)-71122 corresponding to U.S. patent application Ser. No. 08/883,102.) In any of the cases, the alignment is to be made based on the target image i10 if it is detected and identified, or, if not, based on the coordinates of the other targets. As to whether or not the alignment in X, Y-direct ions is completed, the judgement can be made even without detecting all the five target images. That is to say, if the detected and identified target image i10 is within the permissible range, it is judged that the alignment is completed. Upon detecting the target image i10, in addition to the Y coordinate of the rising edge, the center of the luminance point is calculated precisely through processing the edges or the like.

If the luminance points of the target images are identified by repeating the above-identified process on each picture signal carrying one screen data despite the luminance points due to the scattered light, the measuring part 4 is moved to complete the alignment. In the cases where any target images can not be identified, the measuring part 4 is continually moved based on the information obtained previously. When any of the target images are not identified within the predetermined time and thus the alignment is not carried out, it may be arranged so as to inform the examiner of the situation by displaying a screen on the TV monitor 17 which recommends to proceed to an alignment by the joystick 5.

Once the movement of the measuring part 4 brings the target image i10 into the predetermined permissible range, the alignment in X, Y-directions is completed. To make alignment in Z-direction, the measuring part 4 is moved in accordance with the deviation amount obtained based on a signal from the one-dimensional detecting element 63. When the alignment in X, Y-directions as well as in Z-direction is completed, the control circuit 70 automatically generates a measurement starting signal, thereby the measuring system 80 executes the measurement.

Figure 15:
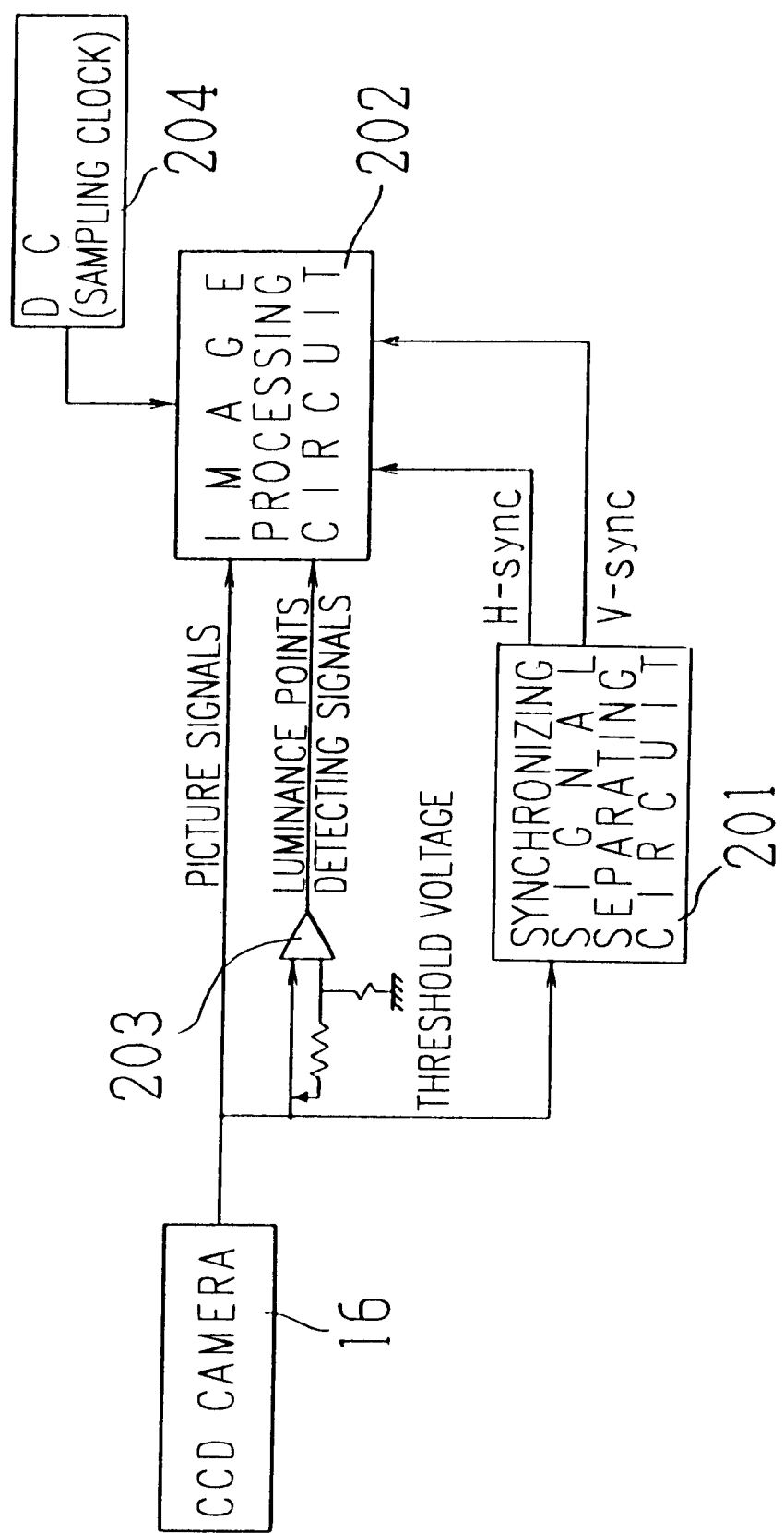
FIG. 15 is a view showing an example of a modification of a luminance point detection.

In the embodiment described above, the picture signals from the CCD camera 16 are once stored into the image memory and then utilized in the luminance point detection. It may be modified, however, so as utilize the picture signals from the CCD camera 16 directly in the luminance point detection. The embodiment applying this modification will be described with reference to FIG. 15 (FIG. 15 only shows the different part of the control system from the one shown in FIG. 3).

The picture signals from the CCD camera 16 include V-sync signals (vertical synchronizing signals) indicating the beginning of each screen and H-sync signals (horizontal synchronizing signals) indicating the beginning of each scanning line. A synchronizing signal separating circuit 201 separates the V-sync signals and the H-sync signals from the picture signals and then inputs the synchronizing signals to the image processing circuit 202. The picture signals from the CCD camera 16 are inputted to a comparator 203. The comparator 203 compares the picture signals to the predetermined threshold signal and thereby detects the signals which exceed the predetermined threshold. The detected signals which carry information about luminance points are inputted to the image processing circuit 202. The image processing circuit 202 is connected to a digital circuit 204 which generates sampling clock signals. The image processing circuit 202 has a function of counting the sampling clock signals and the H-sync signals as well as the luminance point detection signals transmitted from the comparator 203.

The count of the sampling clock signals is initialized by input of the H-sync signals and the counts of the H-sync signals and the luminance point detection signals are initialized by input of the V-syns signals. Accordingly, the counts of the sampling clock signals and the H-sync signals respectively indicate the X coordinate and the Y coordinate of the image on the screen. In addition, the count of the luminance point detection signals indicates the number of luminance points detected in one screen image. It should be noted, however, that the number and the coordinates of luminance points in this case indicate the luminance point edges. This information about the luminance points is stored into the data memory sequentially. Thereafter, the judgements are made in the same manner described in the first embodiment as to whether or not the number of luminance point edges stored in the data memory is within the predetermined available memory (STEP-6) and whether or not the distribution of the luminance point edges exceeds the preset line number LN (STEP-17). In accordance with the judgements, the data corresponding to densely gathered luminance points will be erased, and then the positions of the luminance points are calculated and the target images are identified. As has been described above, if the picture signals from the CCD camera 16 are utilized directly in the luminance point detection, the detection can be speedily performed with providing higher accuracy in the alignment detection.

The foregoing description of the preferred embodiments of the invention has been presented for purposes of illustration and description. It is not intended to be exhaustive or to limit the invention to the precise form disclosed, and modifications and variations are possible in the light of the above teachings or maybe acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus including a measuring part for examining or measuring an eye to be examined by bringing said measuring part into predetermined alignment condition relative to the eye, the apparatus comprising:

target projecting means for projecting a plurality of alignment targets on a cornea of the eye with predetermined arrangement therebetween;

luminance point detecting means for detecting luminance points of which intensity is equal to, or brighter than a predetermined intensity level from luminance points formed on the cornea of the eye upon projecting the alignment targets thereon by said target projecting means;

irregular luminance point detecting means for detecting irregular luminance points based on information about the luminance points detected by said luminance point detecting means; and movement instructing means for instructing movements of said measuring part relative to the eye based on information about the luminance points from which the irregular luminance points detected by said irregular luminance point detecting means are excluded.

2. The ophthalmic apparatus according to claim 1, wherein said irregular luminance point detecting means comprises determining means for determining the luminance points showing abnormal distribution within a predetermined area as irregular ones.

3. The ophthalmic apparatus according to claim 1, wherein said irregular luminance point detecting means comprises:

first judging means for judging whether or not the number of the luminance points detected by said luminance point detecting means is within a predetermined amount;

second judging means for judging whether or not the luminance points detected by said luminance point detecting means distribute within predetermined bounds; and determining means for determining the luminance points which are detected up to a point where the number of the detected luminance points counted sequentially in a vertical direction of the eye reaches the predetermined amount as irregular ones, when said first judging means judges that the number of the detected luminance points exceeds the predetermined amount and said second judging means judges that the detected luminance points distribute within the predetermined bounds.

4. The ophthalmic apparatus according to claim 1, wherein said movement instructing means instructs the movements of said measuring part based on preceding information about the luminance points when valid information is not obtained by exclusion of the irregular luminance points.

5. The ophthalmic apparatus according to claim 1, wherein said luminance point detecting means detects the luminance points, by means of numerous detecting lines perpendicular to a vertical direction of the eye, from the highest detecting line or the lowest detecting line within a predetermined detecting area sequentially; the apparatus further comprising:

judging means for judging whether or not the number of the luminance points detected by said luminance point detecting means exceeds a predetermined amount and whether or not the number of the detecting lines between a detecting line including a position of a first detected luminance point and a detecting line including a position of a luminance point at which the number of the detected luminance points exceeds the predetermined amount exceeds a predetermined line number; and detection control means for controlling said luminance point detecting means so that luminance point is started again from a detecting line updated from a detecting line including a position of a luminance point at which the number of the detected luminance point exceeds the predetermined amount, when the number of the luminance points detected by said luminance point detecting means exceeds the predetermined amount and the number of the detecting lines between a detecting line including a position of a first detected luminance point and a detecting line including a position of a luminance point at which the number of the detected luminance points exceeds the predetermined amount does not exceed the predetermined line number.

6. The ophthalmic apparatus according to claim 5, wherein said detection control means finishes the luminance point detection at the time when the number of the luminance points detected by said luminance point detecting means exceeds the predetermined amount and the number of the detecting lines between a detecting line including a position of a first detected luminance point and a detecting line including a position of a luminance point at which the number of the detected luminance points exceeds the predetermined amount exceeds the predetermined line number.

7. The ophthalmic apparatus according to claim 1, further comprising announcing means for announcing that valid information is not obtained by exclusion of the irregular luminance points detected by said irregular luminance point detecting means in such cases.

8. The ophthalmic apparatus according to claim 1, further comprising memory means for storing positional information about the luminance points detected by said luminance point detecting means, and wherein said irregular luminance point detecting means comprises:

first judging means for judging whether or not an amount of the positional information about the luminance points stored in said memory means exceeds a predetermined amount;

second judging means for judging whether or not the luminance points distribute within predetermined bounds when said first judging means judges that the amount of the positional information about the luminance points exceeds the predetermined amount; and irregular luminance point area determining means for determining an area in which the luminance points distribute as an irregular luminance point area when said second judging means judges that the luminance points distribute within the predetermined bounds.

9. The ophthalmic apparatus according to claim 1, further comprising:

moving means for moving said measuring part relative to the eye; and control means for controlling said moving means based on a signal conveying movement instructions given by said movement instructing means.

10. The ophthalmic apparatus according to claim 1, further comprising moving means for moving said measuring part relative to the eye manually, and wherein said movement instruction means includes display means for displaying a moving direction of said measuring part.

11. An ophthalmic apparatus including a measuring part for examining or measuring an eye to be examined by bringing said measuring part into predetermined alignment condition relative to the eye, the apparatus comprising:

target projecting means for projecting a plurality of alignment targets on a cornea of the eye;

luminance point detecting means for detecting luminance points of which intensity is equal to, or brighter than a predetermined intensity level from luminance points formed on the cornea of the eye upon projecting the alignment targets thereon by said target projecting means;

calculating means for calculating positions of each luminance point when it is judged that the number of the luminance points detected by said luminance point detecting means is equal to, or less than a predetermined amount; and target image locating means for locating positions of each alignment target image by distinguishing the luminance points of the alignment target images from the luminance points due to scattered light based on a result calculated by said calculating means.

12. The ophthalmic apparatus according to claim 11, further comprising movement control means for moving said measuring part relative to the eye based on positional information about the alignment target images obtained by said target image locating means.

13. The ophthalmic apparatus according to claim 11, further comprising:

moving means for moving said measuring part relative to the eye manually; and display means for displaying a moving direction of said measuring part based on positional information about the alignment target images obtained by said target image locating means.

14. The ophthalmic apparatus according to claim 11, further comprising coordinate line number judging means for judging whether or not a coordinate line number from a position of a predetermined luminance point exceeds a predetermined line number when it is judged that the number of the luminance points detected by said luminance point detecting means exceeds the predetermined amount, whereby the positions of each luminance point are calculated by said calculating means based on the detected luminance points and the positions of each alignment target image are located by said target image locating means when said coordinate line number judging means judges that the coordinate line number exceeds the predetermined line number.

15. The ophthalmic apparatus according to claim 14, wherein said luminance point detecting means updates coordinates for luminance point detection from a point where the number of the detected luminance points exceeds the predetermined amount and repeats operations of the luminance point detection when said coordinate line number judging means judges that the coordinate line number counted from the position of the predetermined luminance point does not exceed the predetermined number.

16. The ophthalmic apparatus according to claim 11, further comprising memory means for storing the coordinates of each luminance point when it is judged that the number of the luminance points detected by said luminance point detecting means is within a predetermined storage capacity, whereby the positions of each luminance point are calculated by said calculating means based on positional information about each luminance point stored in said memory means.

17. The ophthalmic apparatus according to claim 11, wherein said target image locating means locates the positions of each alignment target image by comparing the result calculated by said calculating means with standard positional information of the alignment target images.

18. The ophthalmic apparatus according to claim 11, wherein said luminance point detecting means detects an edge of each luminance point.

* * * * *